US009510745B2

United States Patent
Geist et al.

(10) Patent No.: US 9,510,745 B2
(45) Date of Patent: Dec. 6, 2016

(54) LARYNGOSCOPE BLADE

(71) Applicant: Vital Signs, Inc., San Diego, CA (US)

(72) Inventors: Leroy D. Geist, Parker, CO (US); Leroy D. Jutte, Highlands Ranch, CO (US)

(73) Assignee: VITAL SIGNS, INC., Totowa, NJ (US)

( * ) Notice: Subject to any disclaimer, the term of this patent is extended or adjusted under 35 U.S.C. 154(b) by 284 days.

(21) Appl. No.: 14/257,979

(22) Filed: Apr. 21, 2014

(65) Prior Publication Data

US 2014/0221755 A1    Aug. 7, 2014

Related U.S. Application Data

(63) Continuation of application No. 12/573,190, filed on Oct. 5, 2009, now Pat. No. 8,702,598, which is a continuation of application No. 11/726,689, filed on Mar. 22, 2007, now Pat. No. 7,611,459.

(51) Int. Cl.
*A61B 1/267* (2006.01)
*A61B 1/07* (2006.01)
*A61B 1/00* (2006.01)

(52) U.S. Cl.
CPC ............ *A61B 1/267* (2013.01); *A61B 1/00101* (2013.01); *A61B 1/00105* (2013.01); *A61B 1/07* (2013.01)

(58) Field of Classification Search
CPC ......... A61B 1/24; A61B 1/267; A61B 1/2673; A61B 1/2676; A61B 1/273; A61B 1/2733; A61B 1/2736; A61B 1/32; A61B 1/07; A61M 16/0488
See application file for complete search history.

(56) References Cited

U.S. PATENT DOCUMENTS

| 2,354,471 | A |   | 7/1944 | Macintosh |
| 3,760,798 | A |   | 9/1973 | Edinger |
| 4,344,419 | A |   | 8/1982 | Burgin |
| 4,565,187 | A |   | 1/1986 | Soloway |
| 4,570,614 | A | * | 2/1986 | Bauman ............... A61B 1/07 600/193 |
| 4,607,623 | A |   | 8/1986 | Bauman |
| 4,681,094 | A |   | 7/1987 | Rolnick |
| 4,958,624 | A |   | 9/1990 | Stone et al. |

(Continued)

FOREIGN PATENT DOCUMENTS

WO    WO-2005082231 A1    9/2005

OTHER PUBLICATIONS

International Search Report and Written Opinion mailed Aug. 14, 2008 for PCT Application No. PCT/US2008/057549.

(Continued)

*Primary Examiner* — Lynnsy Summitt
(74) *Attorney, Agent, or Firm* — McDermott Will & Emery LLP

(57) ABSTRACT

Embodiments of a laryngoscope blade for being removable mounted to a laryngoscope handle. In some embodiments, the laryngoscope blade may include a blade portion including a proximal end and a distal end provided with an optic window; a base portion including two base halves mounted to each other and to the proximal end of the blade portion such that the proximal end of the blade portion is located between each base half; and an optic light pipe including a proximal end disposed between the two base halves and a distal end extending through the optic window.

20 Claims, 8 Drawing Sheets

(56) References Cited

U.S. PATENT DOCUMENTS

| | | | |
|---|---|---|---|
| 5,060,633 A | * | 10/1991 | Gibson .................. A61B 1/267 600/193 |
| 5,065,738 A | | 11/1991 | Van Dam |
| 5,318,009 A | | 6/1994 | Robinson |
| 5,367,440 A | | 11/1994 | Gruszczynski et al. |
| 5,651,760 A | | 7/1997 | Upsher |
| 5,702,351 A | * | 12/1997 | Bar-Or ................. A61B 1/0676 600/185 |
| 5,800,342 A | | 9/1998 | Lee et al. |
| 5,879,304 A | | 3/1999 | Shuchman et al. |
| 6,013,026 A | | 1/2000 | Krauter et al. |
| 6,213,937 B1 | | 4/2001 | Vivenzio |
| 6,719,688 B2 | | 4/2004 | Pecherer et al. |
| D491,267 S | | 6/2004 | Ashraf |
| 6,890,298 B2 | | 5/2005 | Berci et al. |
| D512,778 S | | 12/2005 | Ashraf |
| 7,128,710 B1 | | 10/2006 | Cranton et al. |
| 7,153,260 B1 | | 12/2006 | Girgis |
| 7,608,040 B1 | | 10/2009 | Dunst |
| 7,695,433 B2 | | 4/2010 | Simons |
| 7,736,304 B2 | | 6/2010 | Pecherer |
| 2003/0018239 A1 | | 1/2003 | Cartledge et al. |
| 2003/0120131 A1 | | 6/2003 | Pecherer et al. |
| 2003/0171654 A1 | | 9/2003 | Skaggs |
| 2007/0129606 A1 | | 6/2007 | Pecherer |

OTHER PUBLICATIONS

International Standard ISO 7376 © ISO 2003.
Search Report and Written from EP Application No. 08732501.5 dated Mar. 6, 2013.
European Office Action for Application No. 08732501.5, dated May 19, 2016, 4 pages.

* cited by examiner

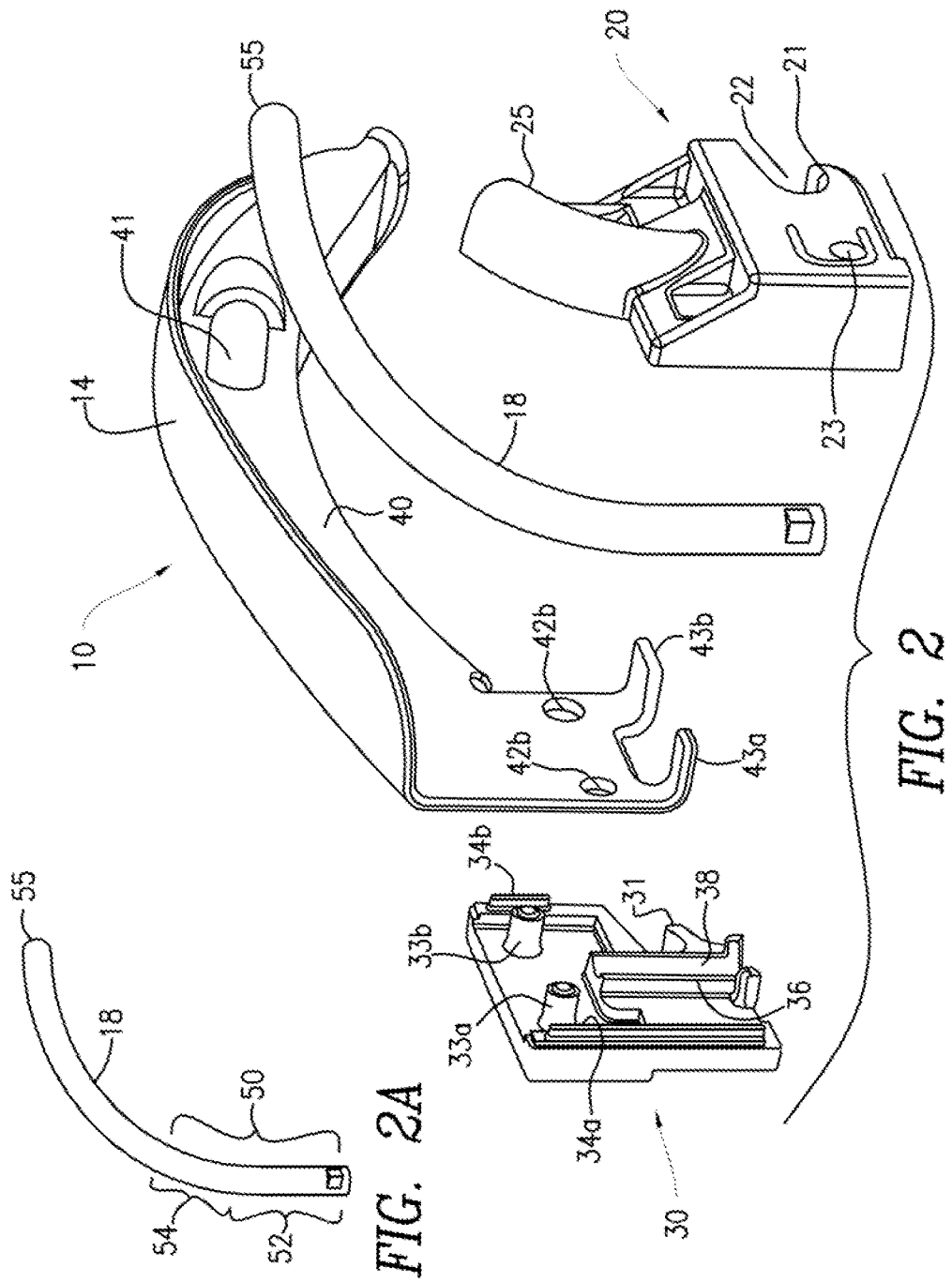

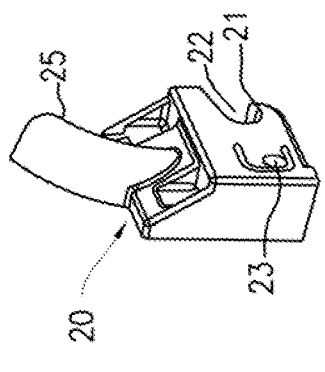
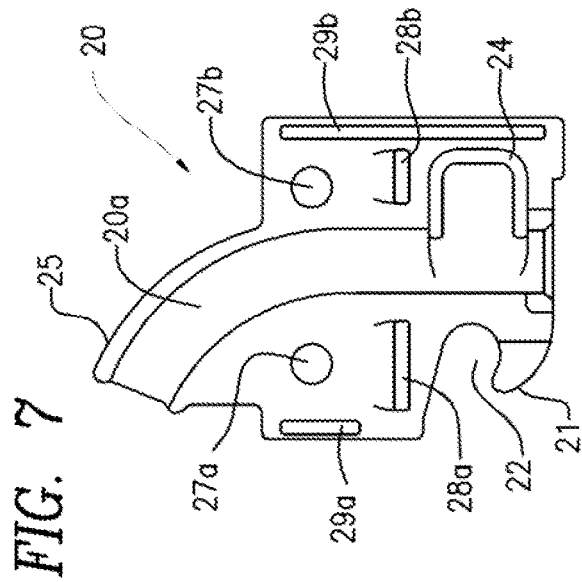
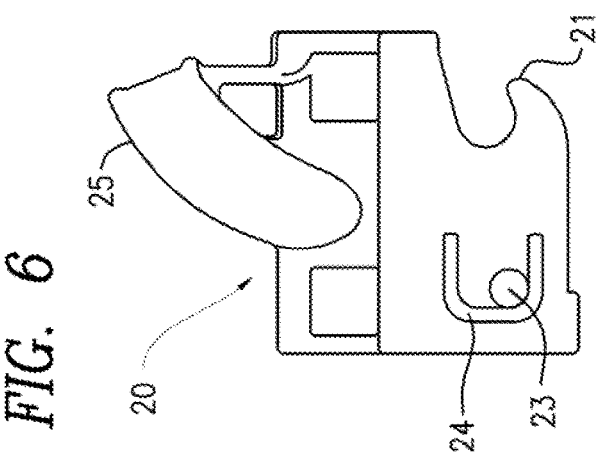
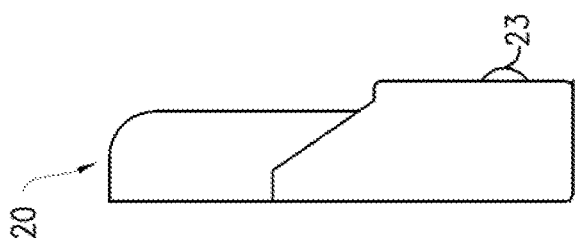

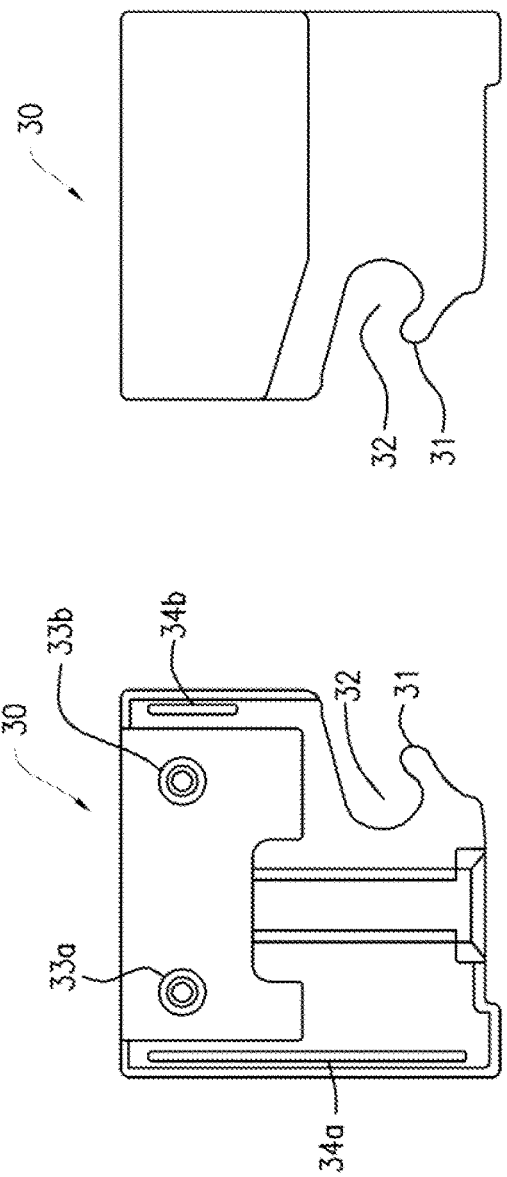
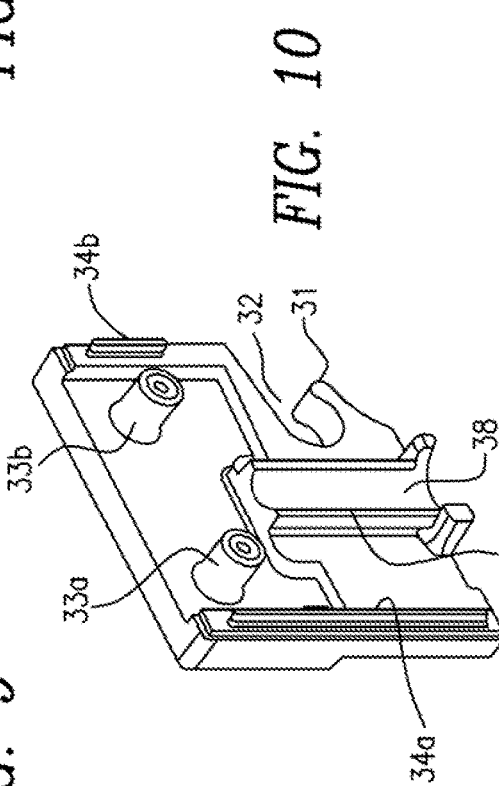
FIG. 8
FIG. 9
FIG. 10

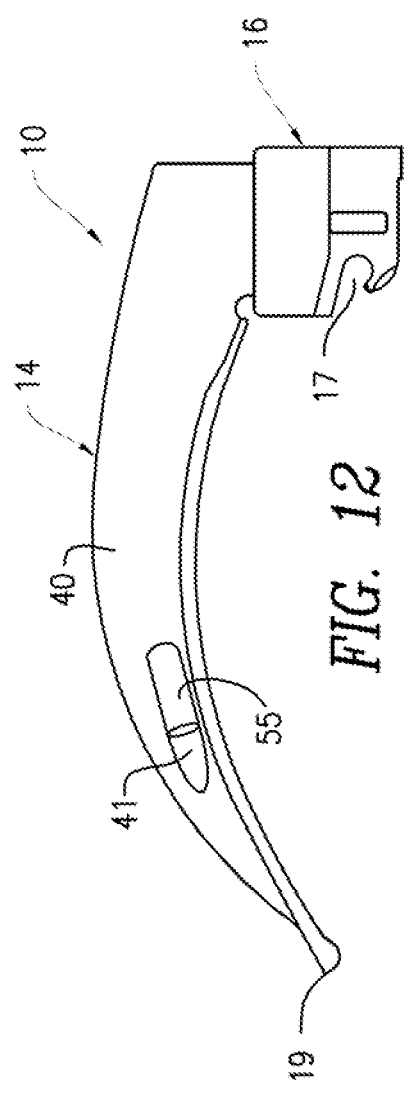
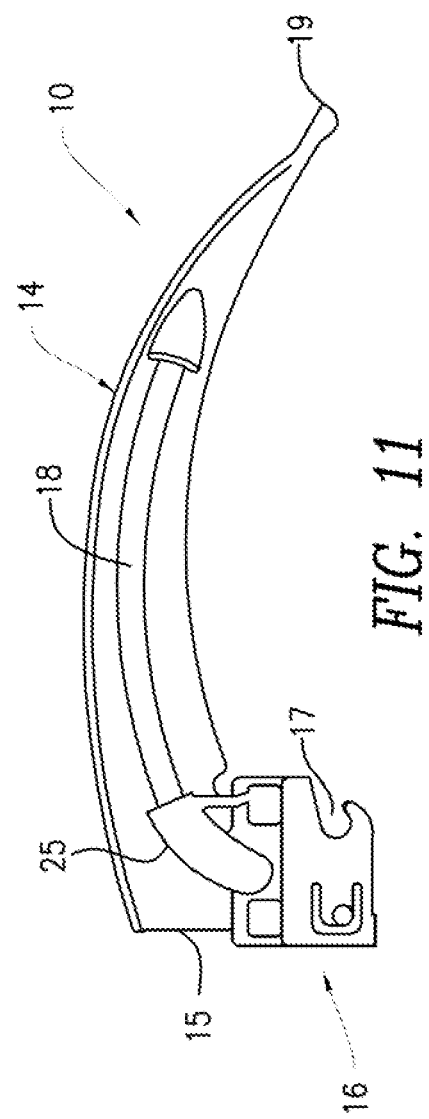

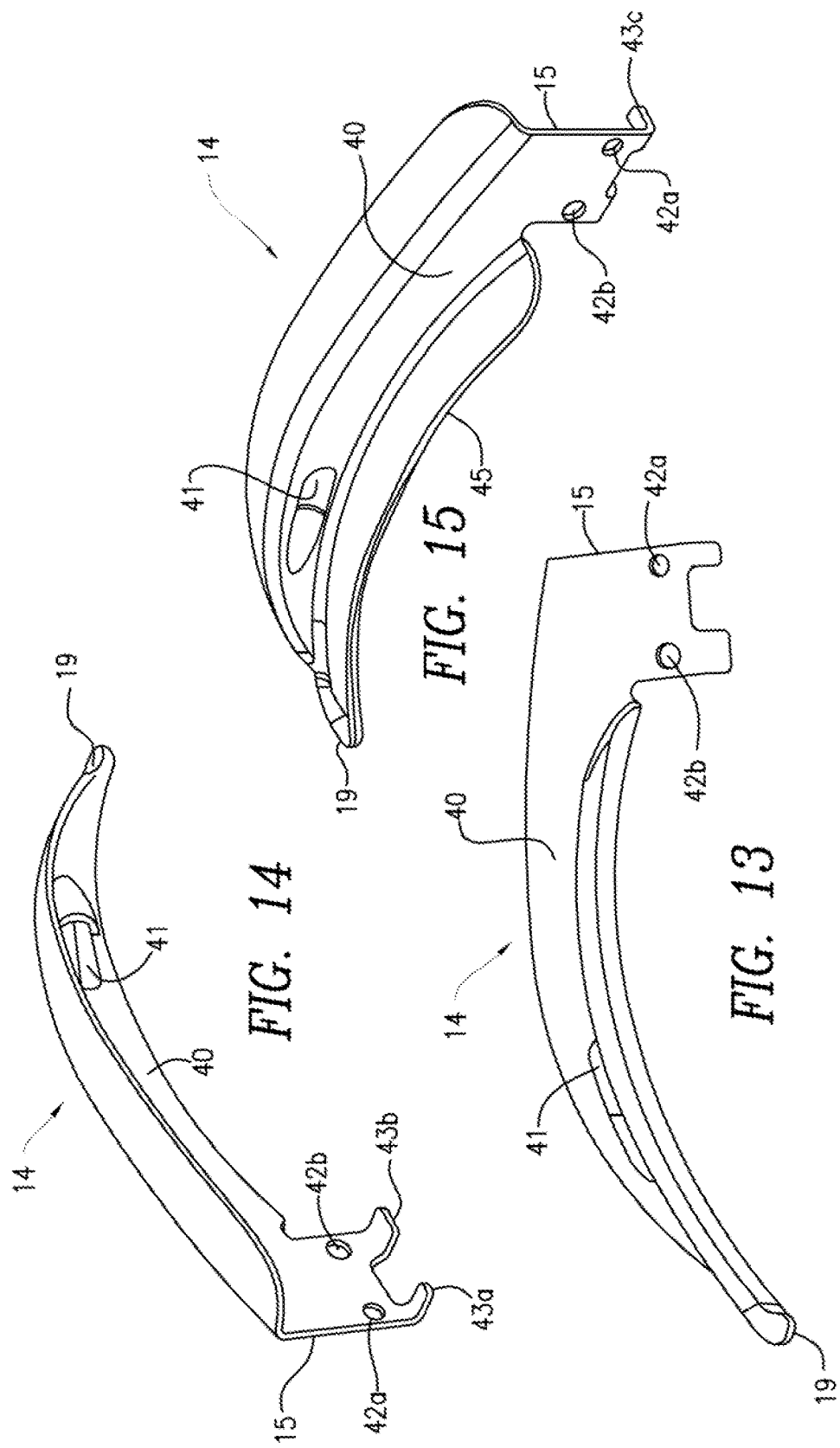

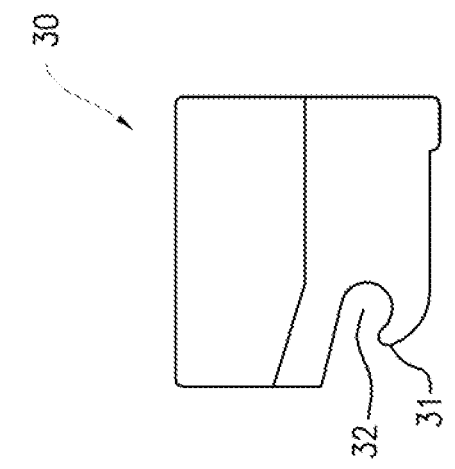
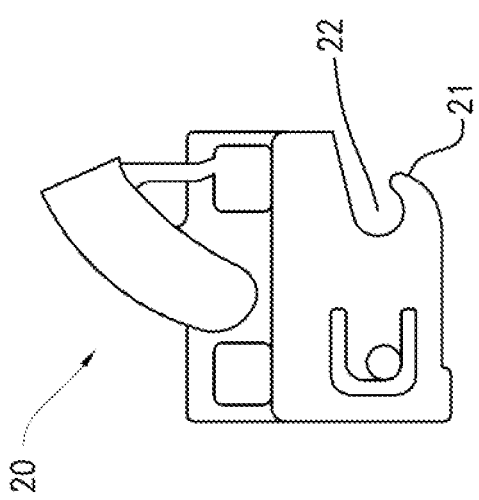
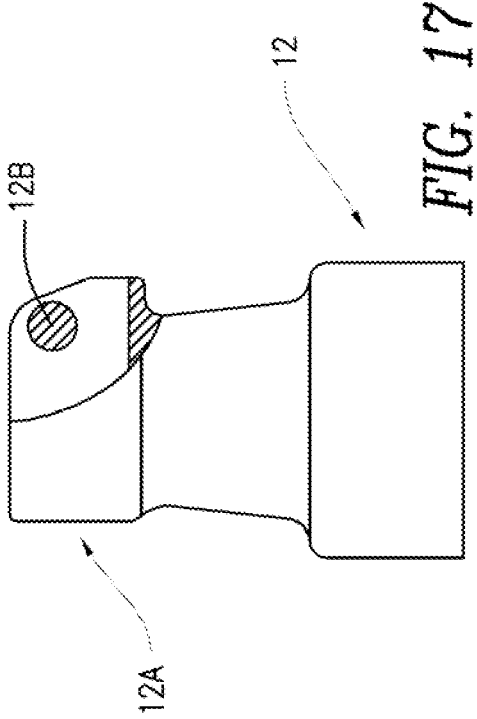

LARYNGOSCOPE BLADE

CROSS-REFERENCE TO RELATED APPLICATIONS

This application is a continuation of U.S. patent application Ser. No. 12/573,190, U.S. Pat. No. 8,702,598, filed Oct. 5, 2009, entitled "Laryngoscope Blade," which is a continuation of U.S. patent application Ser. No. 11/726,689, U.S. Pat. No. 7,611,459, filed Mar. 22, 2007, entitled "Laryngoscope Blade." These patents are incorporated by reference in their entirety herein.

BACKGROUND

This invention relates generally to a laryngoscope blade and more particularly relates to a disposable laryngoscope blade particularly useful with laryngoscope handles commonly referred to as Fiber Illuminated System or Green System Handles. More particularly, this invention relates to a disposable laryngoscope blade of a reduced number of component parts with attendant reduced assembly and manufacturing costs.

Laryngoscope blades are known to the art for examining and visualizing a patient's upper airway and for aiding in placement of an endotracheal tube during intubations. For example, an endotracheal tube is inserted into a patient's trachea to supply oxygen to the patient during a surgical procedure. Generally, a patient's trachea, or wind pipe, is covered by the tongue and the epiglottis which is attached to the base of the tongue at the back of the patient's mouth. For access to the trachea and insertion of the endotracheal tube, the tongue and epiglottis must be lifted to expose the trachea for endotracheal tube insertion. The typical laryngoscope used for this procedure includes a laryngoscope blade mounted to a laryngoscope handle. The laryngoscope blade is inserted under the patient's tongue and upon appropriate movement of the laryngoscope handle the laryngoscope blade lifts the patient's tongue and epiglottis exposing the trachea. Further typically, the laryngoscope blade is provided with an inclined slot which mounts to a hinge pin provided at the upper end of the laryngoscope handle and about which hinge pin the laryngoscope blade pivots to latch into an operating position at the upper end of the laryngoscope handle. As the laryngoscope blade pivots into the operating position, and is locked therein by suitable detents, the laryngoscope blade engages a switch member which closes an energization circuit in the laryngoscope handle causing a light source in the handle to emit light which is transmitted to and through an optic light pipe mounted on the laryngoscope blade to provide light to the end of the laryngoscope blade and to illuminate a patient's exposed trachea to facilitate visualization and insertion of the endotracheal tube into the trachea.

A laryngoscope blade of the type noted above is disclosed in the U.S. Pat. No. 7,128,710 B1, patented Oct. 31, 2006, entitled DISPOSABLE LARYNGOSCOPE BLADES, George D. Granton, et al., inventors; this patent is hereby incorporated herein by reference as if fully reproduced herein. The disclosed laryngoscope blade, as will be noted from FIGS. 1-3 of this patent includes nine separate parts, namely, the blade 26, the heel portion 28, the light rod 34, ball poppets 46, 48 and 42 each of which poppet includes a ball and a springs for a total of the nine component parts. These component parts, particularly the poppets including the balls and springs, require considerable manual labor assembly with attendant unwanted assembly costs and expense.

Accordingly, there is a need in the art for a new and improved laryngoscope blade.

Further, there is a need in the art for a laryngoscope blade of a reduced number of parts and with attendant reduced assembly manufacturing costs which permit the blade to be made and sold at a price attractive and reasonable for a single use or disposable blade.

SUMMARY

It is the object of the present invention to satisfy the foregoing needs in the laryngoscope blade art.

A laryngoscope blade satisfying such need and embodying the present invention may include a laryngoscope blade comprising a blade portion, a base portion and an optic light pipe, the blade portion including a proximal end and a distal end provided with an optic window, the base portion including two base halves mounted to each other and to the proximal end of the blade portion, one of the base halves providing a resilient cantilever latch pin and the other of the base halves providing a rigid hook, the light pipe including a proximal end mounted between the two base halves and a distal end extending through the optic window.

DETAILED DESCRIPTION OF THE DRAWINGS

FIG. 2 is an exploded view of the laryngoscope blade of FIG. 1;

FIG. 2A is a separate view of the optic light pipe shown in FIG. 1;

FIG. 3 is a view of the outside surface of one base half comprising the base portion of the laryngoscope blade of the present invention;

FIG. 4 is a view of the left edge of the base half of FIG. 3;

FIG. 5 is a rear view of the inner surface of the base half of FIG. 3;

FIG. 6 is a perspective view taken from FIG. 5;

FIG. 7 is a perspective view taken from FIG. 7;

FIG. 8 is a view of the outer surface of the other base half comprising the base portion of the laryngoscope blade of the present invention;

FIG. 9 is a view of the inner surface of the base half shown of FIG. 8;

FIG. 10 is a perspective view taken from FIG. 9;

FIG. 11 is a separate view of the laryngoscope blade shown in FIG. 1;

FIG. 12 is a rear view of FIG. 11;

FIG. 13 is a separate view of the blade portion of the laryngoscope blade of the present invention;

FIG. 14 is a rear perspective view of the blade portion shown in FIG. 13;

FIG. 15 is a perspective view taken from FIG. 13;

FIG. 17 is a side view of the upper portion of the laryngoscope handle with portions broken away to show the diameter of the hinge pin;

FIG. 18 is the base half of FIG. 8 reproduced to show the width of the inclined slot provided by the resilient cantilever latch pin; and FIG. 19 is the base half of FIG. 3 reproduced to show the width of the inclined slot provided by the rigid hook.

DESCRIPTION OF THE PREFERRED EMBODIMENT

Figure 1:
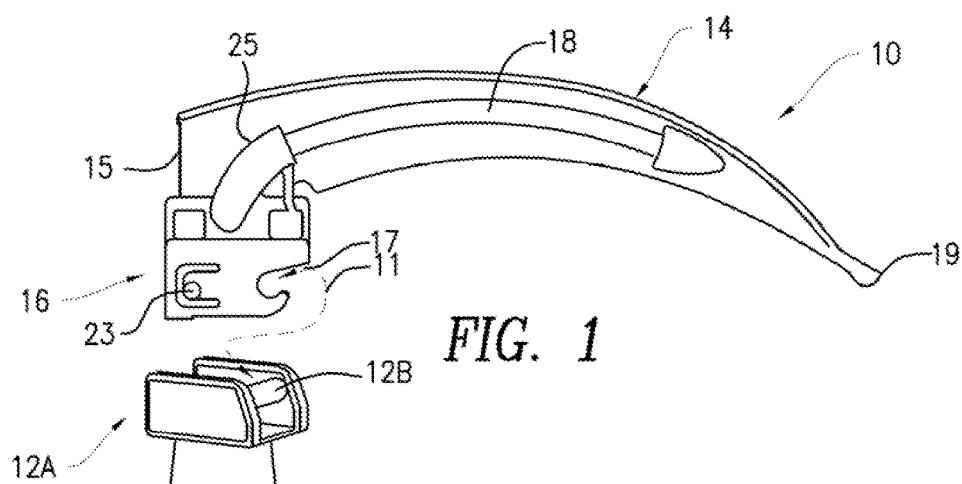
FIG. 1 is a front view of a laryngoscope blade and handle.
Figure 1A:
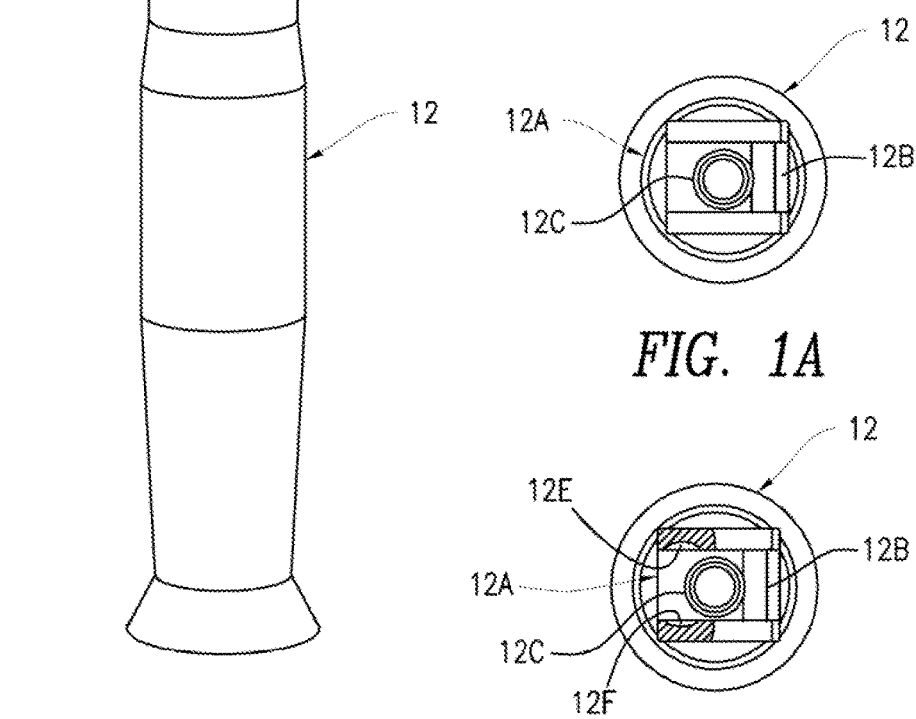
FIG. 1A is a top view of the laryngoscope handle of FIG. 1.
Figure 1B:
FIG. 1B is a diagrammatical illustration of the upper end of the laryngoscope handle of FIG. 1, with portions being broken away, to illustrate opposed locking slots or detents to assist in locking the laryngoscope blade into the operating or on position at the upper end of the laryngoscope handle.

An embodiment of the laryngoscope blade of the present invention is shown in FIG. 1 and indicated by general numerical designation 10, and as indicated by the irregular line 11, is for being mounted removably to the laryngoscope handle indicated by general numerical designation 12 in FIG. 1. The laryngoscope blade 10 includes a blade portion indicated by general numerical designation 14, a base portion indicted by general numerical designation 16 and an optic light pipe 18. The laryngoscope handle 12 may be any suitable laryngoscope handle known to the art and may be, for example, a laryngoscope handle of the type commonly referred to as Fiber Illuminated System or Green System Handles and, by way of further example, may be the laryngoscope handle available from Vital Signs, Inc., 20 Campus Road, Totowa, N.J., and sold under the trademark Greenlight It Solely for purposes of illustration of the use of the laryngoscope blade 10 of the present invention, it will be assumed that the laryngoscope handle 12 of FIG. 1 is the Greenlight II laryngoscope handle, model number 4558GSP, available from Vital Signs, Inc. Accordingly, it will be understood that the laryngoscope handle 12 includes an upper end 12A including a hinge pin 12B and a depressible cylindrical switch element 12C, note FIG. 1A. Referring further to FIG. 1, the laryngoscope blade 10 is mounted removably, as described in detail below, to the handle 12 by hooking or latching the laryngoscope blade base 16 to the hinge pin 12 which is received within the inclined opening 17 provided in the base 16. Upon the hinge pin 128 being received within the inclined opening 17 the laryngoscope blade 10 is pivoted into engagement with the upper end 12A of the laryngoscope handle 12 and locked into the operating or on position by engagement of the resilient ball detent 23 provided on the base portion 16 with the locking slot or detent 12F (FIG. 18) provided at the upper end 12A of the handle 12. Generally, as the laryngoscope blade 10 is pivoted about the hinge pin 12B into the operating position, the base 16 of the laryngoscope blade 10 engages and depresses the circular depressible switch element 12C which then closes an energization circuit (not shown) in the handle 12 to illuminate a light source (not shown) in the handle which emits light which is transmitted through the circular switch element 12C and to and through the optic light pipe 18 to the distal end 19 of the laryngoscope blade to illuminate the opening to a patient's trachea.

Referring further generally to the laryngoscope blade 10 shown in FIGS. 1 and 2, the blade portion 14 is made or formed from a suitable blank of 304 stainless steel using progressive dies of the type known to the art for stainless steel forming. The base portion 16, FIG. 1 is comprised of two base halves as shown in FIG. 2, one base half is indicated by general numerical designation 20 and the other base half is indicated by general numerical designation 30. The base halves are made of ultrasonically weldable material and are ultrasonically welded together by suitable ultrasonic welding apparatus to mount the base halves to each other and to the proximal end 15, FIG. 1, of the blade portion 14. Further generally, it will be understood that in accordance to the present invention, the base half 20 is made of a more rigid material than the material of which the base half 30 is made and conversely, that the base half 30 is made of a more resilient material than the material of which the base half 20 is made. In the preferred embodiment, the base half 20 was made of relatively rigid glass-filled or glass reinforced nylon and the base half 30 was made of relatively resilient un-reinforced nylon; these materials are known ultrasonically weldable materials.

Referring to FIGS, 3-7, and to the detailed structure of the base half 20, the base half 20, made of such glass-filled nylon, includes a rigid hook 21 providing an inclined opening 22, a cantilever ball detent 23 surrounded by a generally U-shaped opening 24 extending through the base half 20, and a curved optic cover 25. Referring to FIG. 5, and to the inner surface of the base half 20, the base half 20 is provided with inwardly extending alignment sockets 27a and 27b, inwardly extending tang sockets 28a and 28b, inwardly extending weld sockets 29a and 29b and an inwardly extending contoured optic channel 20a.

Referring to the detailed structure of the base half 30, and to FIGS. 8-10, the base half 30, made of such un-reinforced nylon, includes a resilient cantilever latch pin 31 providing an inclined opening 32 and, as shown in FIGS. 9 and 10, the inner surface of the base half 30 is provided with a pair of outwardly extending alignment and weld pins 33a and 33b, outwardly extending weld ribs 34a and 34b and an outwardly extending member 36 providing an inwardly extending semi-circular straight optic channel 38.

The blade portion 14 of the laryngoscope blade 10 is shown in detail in FIGS. 12-15 with FIG. 11 being the same showing of the laryngoscope blade 10 of the present invention shown at the top of FIG. 1 but shown again for convenience of reference. Referring specifically to FIGS. 12-15, the metal blade portion 14 includes a medial wall 40 in which an optic window 41 is formed and in which a pair of blade portion attachment thru holes 42a and 42b are formed, The proximal end 15 of the metal blade portion 14 is provided with a pair of perpendicularly, outwardly extending mode distribution and mounting tangs 43a and 43b. As best shown in FIG. 15, the metal blade portion 14 includes a flange 44 extending outwardly perpendicularly from the medial portion 40 and which provides the distal end 19 of the laryngoscope blade 10 and which, as will be understood from FIG. 15, provides a tongue engagement surface 45 which provides the distal end 19 of the laryngoscope blade 10 of FIG. 1. It will be further understood from FIG. 15, that the distal portion of the flange 44 is spoon-shaped to reduce the possibility of trauma to the patient's oral cavity from the intubation process upon the laryngoscope blade 10 of the present invention being utilized to insert an endotracheal tube into a patient's trachea.

Referring to FIG. 2A, the optic light pipe 18 includes a contoured proximal portion 50 which includes a straight proximal end portion 52 and a curved distally adjacent portion 54. The contoured optic channel 20a, FIG. 5, formed in the base half 20 is complimentary in shape to and for receiving the outer side, as viewed in FIG. 2, of the contoured proximal end portion 50 of the optic light pipe 18. Similarly, the straight optic channel 38, FIG. 10, of the base at 30, is complimentary in shape to and for receiving the inner side, as viewed in FIG. 2, of the straight proximal end section 52 of the optic light pipe 18.

In assembly, and prior to ultrasonic welding, and referring primarily to FIG. 2, the outer side of the contoured proximal portion 50 (FIG. 2A) of the light pipe 18 is inserted into the contoured optic channel 20a (FIG. 5) of the base half 20, the distal end 55 of the optic light pipe 18 is inserted through the optic window 41 formed in the blade portion 14 and the tangs 43a and 43b of the blade portion 14 are inserted into the tang sockets 28a and 28b (FIG. 5) provided in the base half 20, the alignment and ultrasonic weld pins 33a and 33b provided on the base half 30 are inserted through the thru holes 42a and 42b formed in the proximal end 15 of the blade portion 15 and into the weld sockets 27a and 27b (FIG. 5) formed in the base half 30, and the weld ribs 34a and 34b formed on the base half 30 are inserted on to the weld sockets 29a and 29b (FIG. 5) formed in the base half 20. In this process the inner half, as viewed in FIG. 2, of the straight distal end 52 (FIG. 2A) of the optic light pipe 18 is received in the straight optic channel 38 formed in the base half 30. Thereafter, the base halves 20 and 30 are ultrasonically welded to each other thereby mounting the base half to each other and to the distal end 15 of the metal blade portion 14 which is captured between the ultrasonically welded base halves. Insertion of the alignment and weld pins 33a and 33b formed on the base half 30 into the weld sockets 27a and 27b formed in the base half 20, and the insertion of the weld ribs 34a and 34b formed on the base half 30 into the weld sockets 29a and 29b formed in the base half 20, align the base halves and the distal end of the blade portion 14 with respect to each other and facilitate ultrasonic welding together of the base halves.

From FIGS. 1, 2 and 11 it will be understood that the curved optic cover 25 of the base half 20 covers the proximal end of the optic light pipe 18 on three sides, the outer three sides as viewed in FIG. 2, and that the medial wall 40 of the blade portion 14 covers the fourth or inner side, as viewed in FIG. 2, of the proximal end of the optic light pipe and hence upon light being transmitted through the optic light pipe 18 to its distal end 55 to illuminate a patient's trachea, the coverage of the distal end of the optic light pipe 18 by the optic cover 25 and the medial wall 40 of the blade portion prevents light from entering, and possibly at least partially blinding, the eyes of the laryngoscope blade 10 user during the patient intubation process.

Referring again to FIG. 1 and to the removable mounting of the laryngoscope blade 10 to the upper end 12a of the laryngoscope handle 12, it will be understood that it is the resilient cantilever latch pin 31, FIGS. 8-10, that wedgedly engages and removably mounts the laryngoscope blade 10 to the hinge pin 12b and thereby to the laryngoscope handle 12 while still permitting pivoting movement therebetween, and that it is the rigid hook 21, FIGS. 3-7, of the base half 20 that loosely engages the hinge pin 12b and withstands the load or force applied to the laryngoscope blade 10 when it engages and lifts up the tongue and epiglottis of a patient to expose the patient's trachea for intubation More particularly, and referring to FIGS. 17-19, the diameter of the hinge pin 12B at the upper end of the handle 12 (FIG. 17) is 4.5 mm, and in the preferred embodiment for the resilient cantilever latch pin 31 (FIG. 18) to wedgedly and removably mount the laryngoscope blade 10 to the handle 12, the width W1 of the inclined slot 32 provided by the resilient cantilever latch pin 31 is 4.0 mm, 0.5 mm smaller that the diameter of the hinge pin 128, and as shown in FIG. 19, the width W2 of the inclined slot 22 provided by the rigid hook 21 is 4.7 mm, 0.2 mm larger than the diameter of the hinge pin 12B, which difference causes the rigid hook 21 to loosely engage the hinge pin 126 so as not to inhibit pivoting movement between the blade 10 and handle 12 and yet permit the rigid hook 21 to engage the hinge pin 12B and withstand the force and load noted above.

Figure 16A:
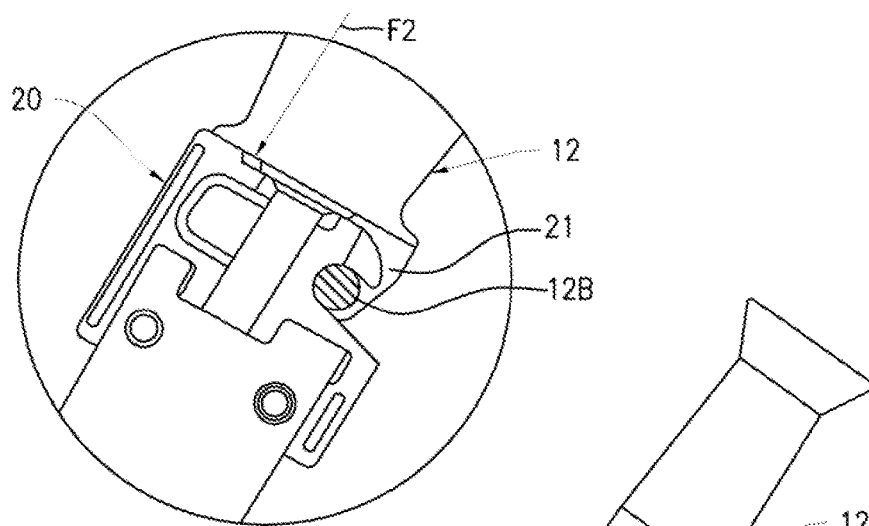
FIG. 16A is an enlarged view of the encircled portion of FIG. 16.
Figure 16:
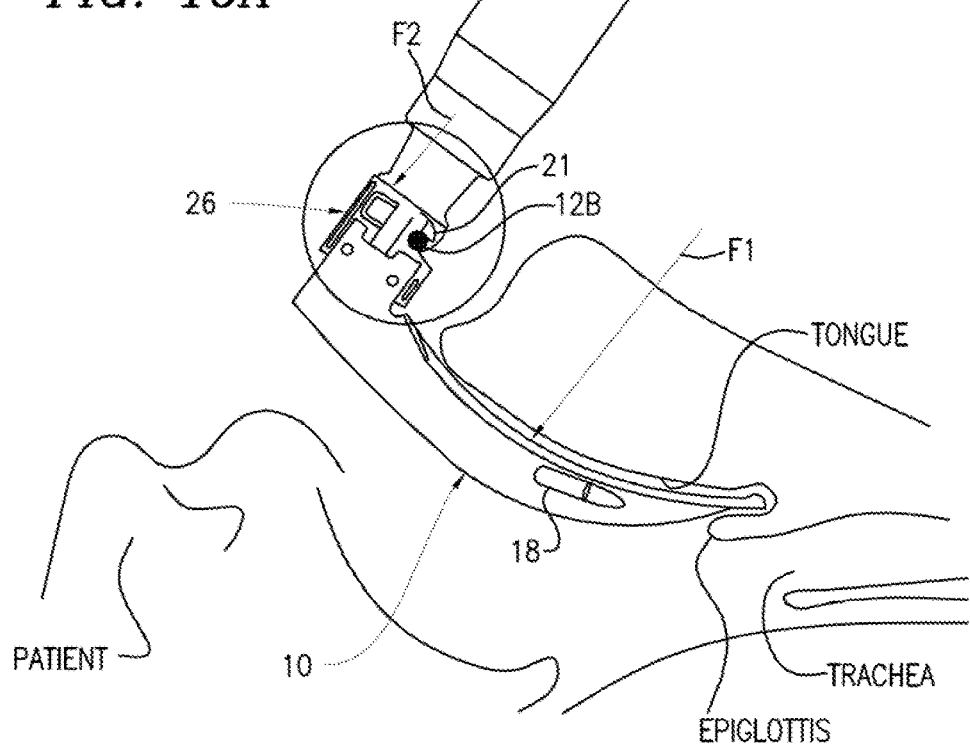
FIG. 16 is a view illustrating the force or load on the laryngoscope blade of the present invention during the lifting of a person's tongue and epiglottis.

With further regard to the above-noted load and force exerted on the laryngoscope blade 10 during use, this loading and force is illustrated in FIGS. 16 and 16A. For insertion of an endotracheal tube (not shown) into the trachea of the patient, the laryngoscope blade 10 (FIG. 16) is inserted under the patient's tongue with the distal end 19 engaging the angled area at which the epiglottis is formed at the back of the tongue, and upon the laryngoscope user, such as a physician, rotating the laryngoscope handle 12 in the direction indicated by the curved arrow 60, the laryngoscope blade 10 lifts the tongue and epiglottis of the patient to expose the trachea for the intubation process. In this tongue and epiglottis lifting procedure, the tongue exerts a force, a reaction force, F1 on the laryngoscope blade 10 and a force, a reaction force F2 (better seen in FIG. 16A) is applied to the base 16 of the laryngoscope blade 10. It will be understood that it is the rigid hook 21 formed on the base half 20 that withstands the forces F1 and F2 and withstands the load applied to the laryngoscope blade 10 by such forces.

It will be understood that the foregoing description of the preferred embodiment of the present invention is merely illustrative thereof and that many variations and modifications may be made in the present invention without departing from the spirit and scope thereof.

The invention claimed is:

1. A laryngoscope blade, comprising:
   a blade portion having a proximal end and an arcuate distal end, the proximal end of the blade portion having a contoured optic channel, the distal end of the blade portion having an optic window;
   a first base half made of a first material and coupled to a second base half made of a second material such that the proximal end is between the first and second base halves, the second material being more resilient than the first material; and
   an optic light pipe having a contoured proximal end and a distal end, the contoured proximal end of the optic light pipe configured to fit in the contoured optic channel, the distal end of the optic light pipe configured to fit in the optic window.

2. The laryngoscope blade of claim 1, wherein the first base half comprises a rigid hook defining an inclined opening.

3. The laryngoscope blade of claim 1, wherein the first base half comprises a cantilever ball detent.

4. The laryngoscope blade of claim 1, wherein the first base half comprises a curved optic cover configured to cover the contoured proximal end of the optic light pipe on three sides.

5. The laryngoscope blade of claim 1, wherein the first base half comprises a plurality of inwardly extending sockets.

6. The laryngoscope blade of claim 1, wherein the second base half comprises a resilient cantilever latch pin defining an inclined opening.

7. The laryngoscope blade of claim 1, wherein the second base half comprises a plurality of outwardly extending pins.

8. The laryngoscope blade of claim 1, wherein the blade portion comprises a medial wall.

9. The laryngoscope blade of claim 8, wherein the optic window is formed in the medial wall.

10. The laryngoscope blade of claim 8, wherein the blade portion comprises an attachment hole in the medial wall.

11. The laryngoscope blade of claim 1, wherein the distal end of the blade portion comprises a mounting tang.

12. The laryngoscope blade of claim 1, wherein the first base half comprises a rigid hook defining a first inclined opening having a first width, the second base half comprises a resilient cantilever latch pin defining a second inclined opening having a second width, and the first width is different than the second width.

13. A laryngoscope blade, comprising:
- a blade portion having a proximal end and an arcuate distal end, the proximal end of the blade portion having a contoured optic channel, the distal end of the blade portion having an optic window;
- a first base half coupled to a second base half such that the proximal end is between inner facing surfaces of the first and second base halves, the second base half defining a straight optic channel; and
- an optic light pipe having a contoured proximal end and a distal end, the contoured proximal end of the optic light pipe configured to fit in the contoured optic channel, the distal end of the optic light pipe configured to fit in the optic window, the optic light pipe configured to fit between the inner facing surfaces of the first and second base halves and in the straight optic channel.

14. The laryngoscope blade of claim 13, wherein the first base half comprises a rigid hook defining an inclined opening.

15. The laryngoscope blade of claim 13, wherein the first base half comprises a cantilever ball detent.

16. The laryngoscope blade of claim 13, wherein the first base half comprises a curved optic cover configured to cover the contoured proximal end of the optic light pipe on three sides.

17. The laryngoscope blade of claim 13, wherein the second base half comprises a resilient cantilever latch pin defining an inclined opening.

18. The laryngoscope blade of claim 17, wherein the optic window is formed in a medial wall of the blade portion.

19. A laryngoscope blade, comprising:
- a blade portion having a flange extending from a medial wall, a proximal end, and an arcuate distal end, the proximal end of the blade portion having a contoured optic channel, the distal end of the blade portion having an optic window;
- a first base half made of a first material and coupled to a second base half made of a second material such that the proximal end is between the first and second base halves, the first base half including an optic cover, the first material being more rigid than the second material, the second material being more resilient than the first material; and
- an optic light pipe having a contoured proximal end and a distal end, the contoured proximal end of the optic light pipe configured to fit in the contoured optic channel, the distal end of the optic light pipe configured to fit in the optic window,
- wherein the optic cover covers the contoured proximal end of the optic light pipe on three sides and the medial wall covers a fourth side of the contoured proximal end of the optic light pipe.

20. The laryngoscope blade of claim 19, wherein the first base half comprises a rigid hook defining a first inclined opening having a first width, the second base half comprises a resilient cantilever latch pin defining a second inclined opening having a second width, and the first width is different than the second width.

\* \* \* \* \*